United States Patent [19]
Sunkel et al.

[11] Patent Number: 4,782,069
[45] Date of Patent: Nov. 1, 1988

[54] 1,4-DIHYDROPIRIDINES AND THEIR USE AS ANTITHROMBOTIC DRUGS

[75] Inventors: Carlos Sunkel; Miguel Fau de Casa-Juana; Fernando Dorrego; Jaime Priego; Pilar Ortega; Javier Cillero, all of Madrid, Spain

[73] Assignee: Alter, S.A., Madrid, Spain

[21] Appl. No.: 51,852

[22] Filed: May 18, 1987

[30] Foreign Application Priority Data

May 28, 1986 [DE] Fed. Rep. of Germany ....... 3617976

[51] Int. Cl.$^4$ .................. C07D 417/12; A61K 31/38
[52] U.S. Cl. .................................. 514/338; 546/270
[58] Field of Search ...................... 546/270; 514/338

[56] References Cited

FOREIGN PATENT DOCUMENTS 0000254 of 0000 European Pat. Off. .
0184841 of 0000 European Pat. Off. .
2652201 of 0000 Fed. Rep. of Germany .

OTHER PUBLICATIONS

Qualitative and Quantitative Structure, Mannhold, et al, Progress in Pharmacology.
European Search Report.
German Search Report.
CA Abstracts, vol. 88, #88:37577m (1987).
CA Abstracts, vol. 105, #105:1082015.

Primary Examiner—Jane T. Fan
Attorney, Agent, or Firm—Ladas & Parry

[57] ABSTRACT

The present invention refers to new 1,4-dihydropyridines, to their obtention processes and to their use as antithrombotic drugs. Said new 1,4-dihdyropyridines have the following general formula (I)

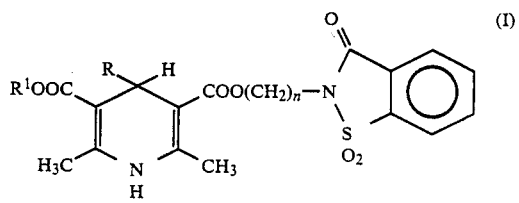

wherein
R represents hydrogen or a saturated or unsaturated alkyl group, with a linear or branched chain of 1 to 8 carbon atoms,
$R^1$ represents an alkyl radical with a linear, branched or cyclic, saturated or unsaturated chain of 1 to 12 carbon atoms, which may be interrupted by an oxygen or by a 2-(N-salicylamido)ethyl group,
n is a number equal to 1 or 2.

These new 1,4-dihydropyridines are obtained by processes based on the Hantzch reaction or on modifications thereof.

11 Claims, No Drawings

1,4-DIHYDROPIRIDINES AND THEIR USE AS ANTITHROMBOTIC DRUGS

FIELD OF THE INVENTION

Nowadays, there is no doubt about the role of platelets in arterial thrombosis (J. M. Sullivan in "Blood platelet function and medicinal chemistry", page 1, Elsevier Biomedical, New York (1984)) and that their main activation processes: adhesion, aggregation and releasing reaction, are fundamental factors in the pathogenesis of thromboembolic disorders, which are one of the most important causes of death in the western world.

The build-up of a platelet aggregate at a damaged area of a blood vessel wall is a primary event in the development of a thrombus. Circulating thromboemboli may appear when these thrombi become emboli or when platelets find aggregating agents in the stream.

A drug capable of directly or indirectly inhibiting these processes would have an obvious interest in the therapeutic control of those pathologic situations wherein platelets are involved and the use thereof would be very useful in the prophylaxis and treatment of arterial thrombosis.

DETAILED DESCRIPTION OF THE INVENTION

A class of 1,4-dihydropyridines has surprisingly shown to exhibit an exceptional activity as platelet activation inhibitors, at the same time as they lack any activity on heart and vascular smooth muscle, this being a characteristic of 1,4-dihydropyridines with calcium-antagonistic activity (A. Lasslo and R. P. Quintana in "Blood platelet function and medicinal chemistry", page 229, Elsevier Biomedical, New York (1984)).

New 1,4-dihydropyridines according to the present invention have the following general formula (I)

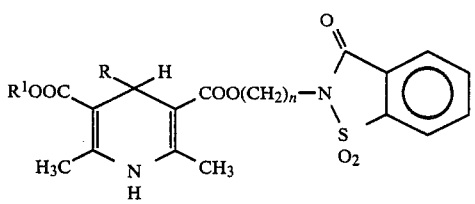

wherein
- R represents hydrogen or a saturated or unsaturated alkyl group with a linear or branched chain of 1 to 8 carbon atoms,
- $R^1$ may represent an alkyl radical with a linear, branched or cyclic chain, either saturated or unsaturated, or 1 to 12 carbon atoms, which may be interrupted by an oxygen atom; or a 2-(N-salicylamido)ethyl group.
- n is a number equal to 1 or 2.

The new compounds may be obtained according to methods based on the Hantzch reaction or on modifications thereof, such as indicated hereinafter:

(a) A compound of formula (II)

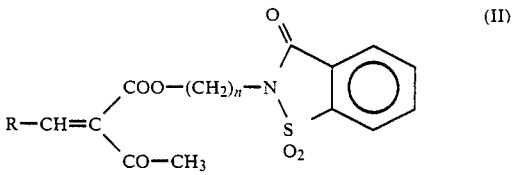

wherein R and n are as previously defined, is made to react with a compound of formula (III)

wherein $R^1$ has been previously defined, so as to yield a compound of formula (I); or (b) A compound of formula (IV)

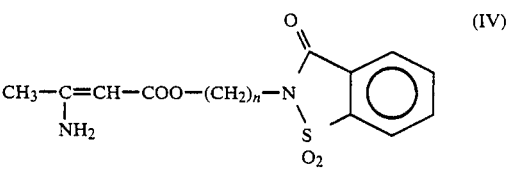

wherein n has been previously defined, is made to react with a compound of formula (V)

wherein R and $R^1$ have been previously defined, so as to yield a compound of formula I, or (c) A compound of formula (VI)

wherein $R^1$ has been previously defined, is made to react with a compound of formula (IV), wherein n has been previously defined and a compound of formula (VII)

wherein R has been previously defined, so as to yield a compound of formula (I), or (d) A compound of formula (VIII)

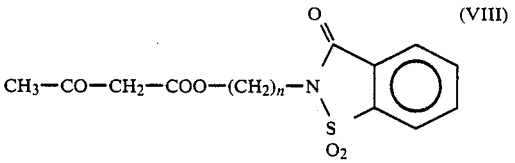

wherein n has been previously defined, is made to react with a compound of formula (III), wherein $R^1$ has been previously defined, and a compound of formula (VII), wherein R has been previously defined, so as to yield a compound of formula (I), or (e) A compound of formula (VI), wherein $R^1$ has been previously defined, is made to react with a compound of formula (VIII), wherein n has been previously defined, and a compound of formula (VII), wherein R has been previously defined, and with NH₃, so as to yield a compound of formula (I).

The present invention also includes the formation of stable salts of compounds of formula I with organic or inorganic, pharmacologically suitable acids.

The reaction conditions used in (a) and (e) variants are as follows:

Water is considered as solvent, as well as all inert organic solvents such as alcohols, e.g. methanol, ethanol, isopropanol and n-butanol; ethers, such as inferior dialkyl ethers, e.g. diethyl ether, ter-buthylmethyl ether or cyclic ethers such as tetrahydrofurane and dioxane; inferior aliphatic carboxylic acids such as acetic and propionic acids; inferior dialkylformamides such as dimethylformamide; inferior alkylnitriles such as acetonitrile; dimethylsulfoxide; liquid heteroaromatic bases, such as pyridine. Solvent mixtures, water included, may also be used. If necessary, the reagents may be made to react without solvents.

The reaction temperature may vary between 20° and 150° C., preferably between 50° and 100° C. The reaction is usually carried out at the boiling temperature of the solvent used.

The reaction may be conducted at the normal pressure, but also under high pressure. It is usually conducted at the normal pressure.

The time of the reaction ranges from 45 minutes to 10 hours.

According to the invention, the separation and isolation of the product yielded along the reaction are carried out by techniques usually used for this purpose, the product being able to be submitted to a conventional purification such as recrystallization, distillation or chromatography.

The present invention is illustrated by the following non-limitative examples:

EXAMPLE 1

2-{N-(1,2-benzisothiazolyl-3(2H)one-1,1-dioxide)} ethyl 2,6-dimethyl-5-ethoxycarbonyl-4-methyl-1,4-dihydropyridine-3-carboxylate.

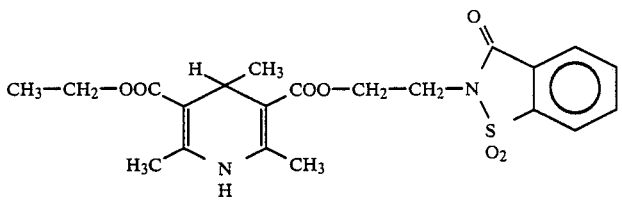

(A) 2-{N-(1,2-benzisothiazolyl-3(2H)one-1,1-dioxide)}-ethyl acetylacetate.

10.1 ml (11.1 g; 0.13 mol) of Diketene are slowly added, under agitation, onto a mixture comprising 30 g (0.13 mol) of N-(2-hydroxyethyl)-1,2-benzisothiazol-3(2H)one-1,1-dioxide and 0.2 ml of triethylamine previously heated to about 80° C. The addition speed is adjusted so that the reaction temperature stays between 85° and 90° C. Once the addition is finished, the reaction mixture is kept under agitation at 90° C. for 3 hours. After said period of time, the resulting solution is diluted with 500 ml of CH₂Cl₂, washed with H₂O (2×500 ml), decolorized by passing it through Active Carbon-Infusoria Earth and dried over anhydrous Na₂SO₄. Finally, the evaporation of the solvent under low pressure leads to an oily yellow liquid that solidifies slowly so as to yield finally a crystalline white solid with melting point: 62°-3° C. (ethanol recrystallization). The reaction yield is 88%.

I.R. Spectrum (NaCl) $\nu(cm^{-1})$: 2980, 1770, 1740, 1720, 1460, 1420, 1330, 1260, 1190, 1150, 1050, 1000, 960, 750, 670, 610.

M.N.R. Spectrum (CDCl₃) p.p.m.: 7.8 (4H,m); 4.5 (2H,t); 4 (2H,t); 3.5 (2H,s); 2.2 (3H,s).

(B) 2-{N-(1,2-benzisothiazolyl-3(2H)one-1,1-dioxide)} ethyl 2,6-dimethyl-5-ethoxycarbonyl-4-methyl-1,4-dihydropyridine-3-carboxilate.

A mixture comprising 13.05 g (0.04 mol) of 2-{N-(1,2-benzisothiazolyl-3(2H)one-1,1-dioxide)} ethyl acetylacetate, 5.41 g (0.04 mol) of ethyl 3-aminocrotonate and 2.4 ml (1.85 g; 0.04 mol) of acetaldehyde in 50 ml of ethanol, is heated under reflux with agitation for 10 hours. After cooling to −10° C. the resulting solution, a light yellow solid with melting point: 144°-6° C. (ethyl acetate recrystallization) is obtained. The reaction yield is 81%.

| Analysis for C₂₁H₂₄N₂O₇S: | | | |
|---|---|---|---|
| | % C | % H | % N |
| Calculated | 56.24 | 5.39 | 6.25 |
| Found | 55.96 | 5.54 | 5.98 |

I.R. Spectrum (KBr): $\nu(cm^{-1})$: 34,00 3130, 2980, 2940, 1750, 1700 1620, 1480, 1450, 1340, 1330, 1300, 1280, 1220, 1180, 1100, 1060, 1000, 830, 790, 770, 750, 680, 610.

M.N.R. Spectrum (δ, DMSO-D₆): p.p.m.: 8.5 (1H,sa); 8 (4H,m); 4.6 to 3.6 (7H,m); 2.2 (6H,s); 1.2 (3H,t); 0.9 (3H,d).

EXAMPLE 2

2-{N-(1,2-benzisothiazolyl-3(2H)one-1,1-dioxide)} ethyl 2,6-dimethyl-4-methyl-5-methoxycarbonyl-1,4-dihydropyridine-3-carboxylate.

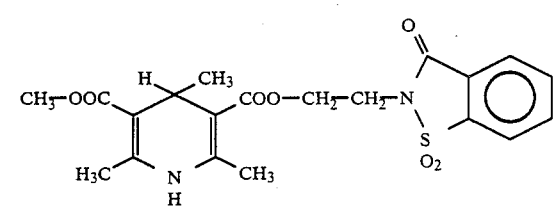

A mixture comprising 15 g (0.05 mol) of 2{N-(1,2-benzisothiazolyl-3(2H) one-1,1-dioxide)} ethyl acetylacetate (obtained according to the process given in example 1), 5.55 g (0.05 mol) of methyl 3-aminocrotonate and 2.7 ml (2.12 g; 0.05 mol) of acetaldehyde in 50 ml of ethanol is heated under reflux with agitation for 10 hours. After evaporation of the solvent under low pressure, the resulting residue is solved into 15 ml of ethyl acetate under boiling and this solution is cooled to 5° C. A yellowish solid with melting point: 146°-9° C. (ethyl acetate recrystallization) is thus obtained. The reaction yield is 58%.

Analysis for $C_{20}H_{22}N_2O_7S$

|  | % C | % H | % N | % S |
|---|---|---|---|---|
| Calculated | 55.29 | 5.10 | 6.45 | 7.38 |
| Found | 55.06 | 5.25 | 6.34 | 7.18 |

I.R. Spectrum (KBr): $\nu(cm^{-1})$: 3380, 3100, 3030, 2960, 1750, 1700, 1670, 1500, 1450, 1430, 1330, 1260, 1220, 1180, 1140, 1090, 1060, 770, 750, 670.

M.N.R. Spectrum ($\delta$, $CDCl_3+DMSO-D_6$): p.p.m.: 8.2 (1H,sa); 7.9 (4H,m); 4.4 (2H,td); 4.1 (3H,td); 3.6 (3H,s); 2.2 (6H,s); 0.8 (3H.d).

EXAMPLE 3

2{N-(1,2-benzisothiazolyl-3(2H)one-1,1-dioxide)} ethyl 2,6-dimethyl-4-methyl-1,4-dihydropyridine-5-carboxylate.

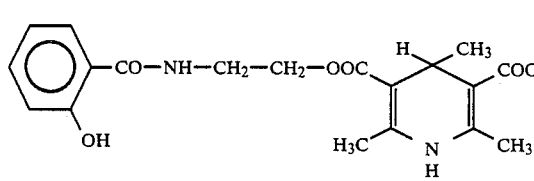

A mixture comprising 15 g (0.05 mol) of 2-{N-(1,2-benzisothiazolyl-3(2H)one-1,1-dioxide)} ethyl acetylacetate (obtained according to the process described in example 1), 12.73 g (0.05 mol) of 2-(N-salicylamido)ethyl 3-aminocrotonate and 2.7 ml (2.12 g; 0.05 mol) of acetaldehyde in 50 ml of ethanol, is heated under reflux with agitation for 10 hours. After the evaporation of the solvent under low pressure, the resulting residue is solved into 10 ml of ethanol under boiling and this solution is cooled to $-10°$ C. A slightly yellow solid with melting point: 86°-90° C. is thus obtained. The reaction yield is 46%.

Analysis for $C_{28}H_{29}N_3O_9S$

|  | % C | % H | % N | % S |
|---|---|---|---|---|
| Calculated | 57.63 | 5.01 | 7.20 | 5.49 |
| Found | 57.42 | 5.12 | 6.94 | 5.23 |

I.R. Spectrum (KBr) $\nu(cm^{-1})$: 3380, 3100, 2980, 1750, 1700, 1650, 1610, 1560, 1500, 1350, 1310, 1220, 1200, 1150, 1110, 1070, 780, 760, 680.

M.N.R. Spectrum ($\delta$, $DMSO-D_6$): p.p.m.: 12.3 (1H,sa); 8.8 (1H,m); 8.6 (1H,m); 8.6 to 6.8 (8H,m); 4.7 to 3.6 (9H,m); 2.3 (6H,s); 1(3H,sda).

EXAMPLE 4

{N-(1,2-benzisothiazolyl-3(2H)one-1,1-dioxide)} methyl 2,6-dimethyl-4-methyl-5-methoxycarbonyl-1,4-dihydropyridine-3-carboxylate.

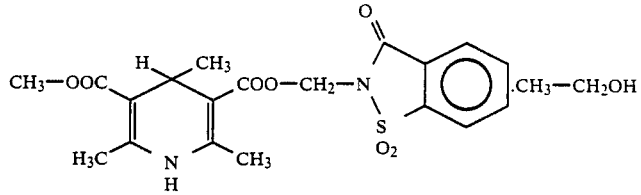

(A) {N-(1,2-benzisothiazolyl-3(2H)one-1,1-dioxide)} methyl acetylacetate.

55.5 ml (60.9 g; 0.72 mol) of diketene are slowly added, with agitation, onto a suspension consisting of 128.69 g (0.60 mol) of N-hydroxymethyl-1,2-benzisothiazol-3(2H)one-1,1-dioxide and 9.66 g (0.03 mol) of mercuric acetate in 138 ml of acetic acid. Once the addition is finished, the resulting mixture is kept with agitation at room temperature for 8 hours and then it stands resting overnight. The resulting solid is filtered, washed with $H_2O$ and dried, thereby obtaining a white product with melting point: 111°-3° C. The reaction yield is 89%.

I.R. Spectrum (KBr): $\nu(cm^{-1})$: 3100, 3040, 1770, 1760, 1730, 1600, 1430, 1420, 1340, 1240, 1190, 1140, 1040, 1010, 970, 800, 750, 680, 650, 610.

M.N.R. Spectrum ($\delta$, $CDCl_3+DMSO-D_6$): p.p.m.: 8 (4H,m); 5.8 (2H,s); 3.6 (2H,s); 2.2 (3H,s).

(B) {N-(1,2-benzisothiazolyl-3(2H)one-1,1-dioxide)} methyl 2,6 dimethyl-4-methyl-5-methoxycarbonyl-1,4-dihydropyridine-3-carboxylate.

A mixture comprising 15 g (0.05 mol) of {N-(1,2-benzisothiazolyl-3(2H)one-1,1-dioxide)} methyl acetylacetate, 5.81 g (0.05 mol) of methyl 3-aminocrotonate and 3 ml (2.22 g; 0.05 mol) of acetaldehyde in 50 ml of ethanol is heated under reflux with agitation for 8 hours. After said period of time is over, the resulting solution is cooled to $-10°$ C., thereby obtaining a yellow solid with melting point: 89°-92° C. (ethanol recrystallization). The reaction yield is 58%.

Analysis for $C_{19}H_{20}N_2O_7S.C_2H_6O$:

|  | % C | % H | % N | % S |
|---|---|---|---|---|
| Calculated | 54.07 | 5.62 | 6.00 | 6.87 |
| Found | 53.87 | 5.49 | 6.20 | 6.78 |

I.R. Spectrum (KBr): $\nu(cm^{-1})$: 3460, 3400, 3120, 3000, 1760, 1700, 1660, 1500, 1440, 1390, 1350, 1260, 1220, 1190, 1140, 1100, 1030, 1000, 770, 750, 680.

M.N.R. Spectrum ($\delta$, $CDCl_3$): p.p.m.: 7.9 (4H,m); 6.9 (1H,s); 5.9 (2H,s); 3.7 (6H,m+s); 2.8 (1H,s); 2.3 (6H,s); 1.3 to 0.8 (3H+3H, t+d).

EXAMPLE 5

{N-(1,2-benzisothiazolyl-3(2H)one-1,1-dioxide)} methyl 2,6-dimethyl-5-ethoxycarbonyl-4-methyl-1,4-dihydropyridine-3-carboxylate.

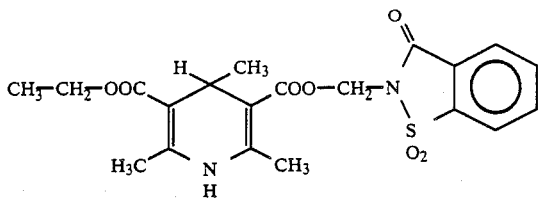

A mixture comprising 15 g (0.05 mol) of {N-(1,2-benzisothiazolyl-3(2H)one-1,1-dioxide)} methyl acetylacetate (obtained according to the process given in example 4), 6.52 g (0.05 mol) of acetaldehyde in 50 ml of ethanol is heated under reflux for 8 hours. Once said period of time is over, the resulting solution is cooled to $-10°$ C., thereby obtaining a solid with melting point: 162°–4° C. (ethyl acetate and aqueous ethanol recrystallization). The reaction yield is 40%.

| Analysis for $C_{20}H_{22}N_2O_7S$: | | | | |
|---|---|---|---|---|
|  | % C | % H | % N | % S |
| Calculated | 55.30 | 5.10 | 6.45 | 7.38 |
| Found | 55.00 | 5.12 | 6.47 | 7.55 |

I.R. Spectrum (KBr): $\nu(cm^{-1})$: 3380, 2960, 1770, 1710, 1680, 1490, 1350, 1290, 1260, 1220, 1200, 1140, 1070, 1030, 770, 750, 680.

M.N.R. Spectrum ($\delta$, DCCl$_3$): p.p.m.: 7.9 (4H,m); 6.6 (1H,sa); 5.9 (2H,s); 4.3 to 3.6 (2H+1H, 2c); 2.3 (6H,s); 1.3 (3H,t); 1 (3H,d).

EXAMPLE 6

2-{N-(1,2-benzisothiazolyl-3(2H)one-1,1-dioxide)} ethyl 4-n-butyl-2,6-dimethyl-5-methoxycarbonyl-1,4-dihydropyridine-3-carboxylate.

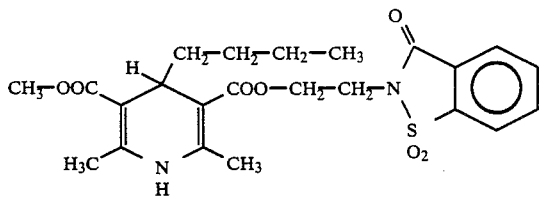

A mixture comprising 20 g (0.06 mol) of 2-{N-(1,2-benzisothiazolyl-3(2H)one-1,1-dioxide)} ethyl acetylacetate (obtained according to the process given in example 1), 7.40 g (0.06 mol) of methyl 3-aminocrotonate and 6.9 ml (5.53 g; 0,06 mol) of valeraldehyde in 65 ml of ethanol, is heated under reflux with agitation for 10 hours. After said time is over, the solvent is evaporated under low pressure and the resulting residue is solved into 25 ml of ethyl acetate under boiling and cooled at room temperature. A light yellow solid is thus obtained, with melting point: 119°–121° C. (ethyl acetate recrystallization). The reaction yield is 68%.

I.R. Spectrum (KBr): $\nu(cm^{-1})$: 3340, 3100, 2960, 2920, 1740, 1710, 1660, 1490, 1450, 1350, 1270, 1220, 1190, 1140, 1090, 1010, 970, 790, 770, 760, 740, 670, 610.

M.N.R. Spectrum ($\delta$, DMSO-D$_6$): p.p.m.: 8.5 (1H,sa); 8.2 to 7.8 (4H,m); 4.4 to 3.3 (5H+3H, m+s); 2.2 (6H,s); 1.2 to 0.5 (9H,m).

The antiplatelet activity of the described compounds was measured by an "in-vitro" activity assay and an "in-vivo" thrombosis model in the mouse, which are indicated hereinafter.

(A) "IN VITRO" AGGREGATION ON HUMAN PLATELETS (Born, G.V.R., Nature 194:927 (1962)).

Citrated human blood was used, from which platelet-rich plasma (PRP) was prepared. 450 ul PRP aliquots were incubated at 37° C. with the assayed compounds at a single concentration of $10^{-4}$M for 15 minutes. Aggregating agents (2 ug/ml collagen and 2.5 uM ADP) were added in a 50 ul volume and the aggregation was measured as optical density decrease in the platelet suspension.

Simultaneously to the collagen aggregation, the effect on the releasing reaction that measures the ATP secretion from activated platelets was determined (Feinman, R. D., Lubowsky, J., Charo, I. F., Zabinski, M. P.; J. Lab. Clin. Med. 90:125 (1977)).

The results are expressed in Table 1.

(B) "IN VIVO" THROMBOSIS MODEL (DiMinno, G., Silver, M. J.; J. Pharmacol. Exptl. Ther. 225:57 (1983)).

This is a suitable method for the screening of antithrombotic agents having a primary activity on platelet thormboembolism.

CD-1 Charles River male mice weighing 30 g were used. They received and i.v. injection of 15 ug collagen and 1.8 ug epinephrine in 100 ul of isotonic solution. About the 90% of the animals died or were paralysed for more than 15 minutes.

Drugs were intraperitoneally administered as a suspension in 0.5% carboxymethylcellulose and the protecting effect thereof against thrombosis was measured one to four hours after the administration.

The results are expressed in Table 2.

TABLE 1

EFFECT OF THE COMPOUNDS ON HUMAN PRP "IN VITRO" AGGREGATION AND RELEASING REACTION.

| Compound according to example No. | INHIBITION % | | |
|---|---|---|---|
|  | ADP | Collagen | Releasing Reaction |
| 1 | 12 | 84 | 80 |
| 2 | 20 | 48 | 43 |
| 3 | 15 | 24 | 18 |
| 4 | 5 | 14 | 19 |
| 5 | 20 | 55 | 51 |
| 6 | 8 | 15 | 29 |
| DIPYRIDAMOL | 17 | 21 | 38 |

TABLE 2

| Compound according to Example No. | Protection % | |
|---|---|---|
|  | 30 mg/kg | 60 mg/kg |
| 1 | 50 | 70 |
| 2 | 0 | 42 |
| 3 | 62 | 62 |
| 4 | 20 | 20 |
| 5 | 30 | 50 |
| 6 | 12 | 34 |
| DIPYRIDAMOL | 30 | 30 |

We claim:
1. A 1,4-dihydropyridine of formula I

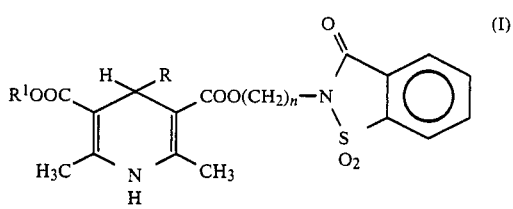

wherein, R represents hydrogen or a saturated alkyl group with a linear or branched chain of 1 to 8 carbon atoms, $R^1$ represents an alkyl group with a linear, or branched, saturated chain of 1 to 12 carbon atoms, or cyclic chain of 3–12 carbon atoms, or a 2-(N-salicylamido) ethyl group, and n is a number equal to 1 or 2.

2. The compound as in claim 1 wherein R=methyl, $R^1$=ethyl and n=2.

3. The compound, as n claim 1 wherein R=methyl, $R^1$=methyl and n=2.

4. The compound, as in claim 1 wherein R=methyl, R1=2-(N-salicylamido) ethyl and n=2.

5. The compound, as in claim 1 wherein R=methyl, $R^1$=methyl and n=1.

6. The compound, as in claim 1 wherein R=methyl, $R^1$=ethyl and n=1.

7. The compound, as in claim 1 wherein R=n-butyl, $R^1$=methyl and n=2.

8. An antithrombotic composition comprising an effective amount of a compound of formula I

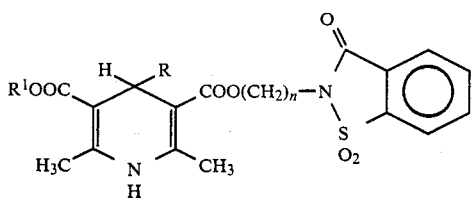

wherein, R represents hydrogen or a saturated alkyl group with a linear or branched chain of 1 to 8 carbon atoms, $R^1$ represents an alkyl group with a linear, or branched, saturated chain of 1 to 12 carbon atoms, or cyclic chain of 3–12 carbon atoms, or a 2-(N-salicylamido) ethyl group, and n is a number equal to 1 or 2 and a pharmaceutically acceptable carrier therefor.

9. A method for inhibiting platelet activation, comprising administering to a patient in need of such treatment an effective amount of a composition comprising

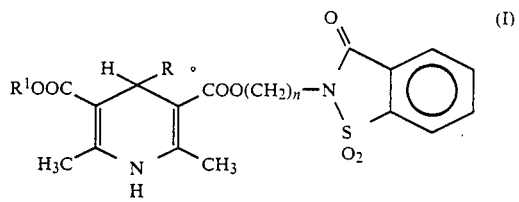

wherein R represents hydrogen or a saturated alkyl group with a linear or branched chain of 1 to 8 carbon atoms, $R^1$ represents an alkyl group with a linear, or branched, saturated chain of 1 to 12 carbon atoms, or a cyclic chain of 3–12 carbon atoms or a 2-(N-salicylamido) ethyl group, and n is a number equal to 1 or 2 and a pharmaceutically acceptable carrier therefore.

10. A method for treating arterial thrombosis comprising administering to a patient in need of such treatment an effective amount of a composition comprising

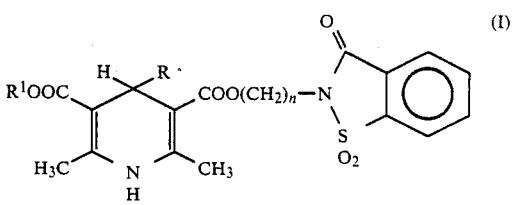

wherein, R represents hydrogen or a saturated alkyl group with a linear or branched chain of 1 to 8 carbon atoms, $R^1$ represents an alkyl radical with a linear, or branched, saturated chain of 1 to 12 carbon atoms, or a cyclic chain of 3–12 carbon atoms, or a 2-(N-salicylamido) ethyl group, and n is a number equal to 1 or 2 and a pharmaceutically acceptable carrier therefor.

11. A method for treating patients requiring inhibition of platelet activators while failing to have activity on heart and vascular smooth muscle comprising administering to the patient in need of treatment of composition comprising

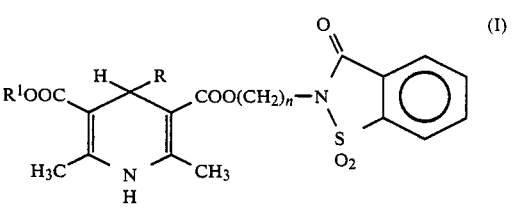

wherein, R represents hydrogen or a saturated alkyl group with a linear or branched chain of 1 to 8 carbon atoms, $R^1$ represents an alkyl group with a linear, or branched or, saturated chain of 3–12 carbon atoms chain of 1 to 12 carbon atoms, or a 2-(N-salicylamido) ethyl group, and n is a number equal to 1 or 2 and pharmaceutically acceptable carrier therefor.

* * * * *